United States Patent
Zou et al.

(10) Patent No.: US 9,329,140 B2
(45) Date of Patent: May 3, 2016

(54) APPARATUS AND METHOD FOR REDUCING X-RAY FLUX IN SPECTRAL CT

(71) Applicants: Kabushiki Kaisha Toshiba, Minato-ku (JP); Toshiba Medical Systems Corporation, Otawara-shi (JP)

(72) Inventors: Yu Zou, Naperville, IL (US); Yuexing Zhang, Naperville, IL (US); Xiaolan Wang, Buffalo Grove, IL (US)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 187 days.

(21) Appl. No.: 13/922,922

(22) Filed: Jun. 20, 2013

(65) Prior Publication Data

US 2014/0376689 A1  Dec. 25, 2014

(51) Int. Cl.
*G01N 23/04* (2006.01)

(52) U.S. Cl.
CPC .................................... *G01N 23/046* (2013.01)

(58) Field of Classification Search
CPC ..... A61B 6/488; A61B 6/4241; A61B 6/4035
See application file for complete search history.

(56) References Cited

U.S. PATENT DOCUMENTS

| 9,101,273 | B2 | 8/2015 | Gagnon et al. |
| 2005/0089135 | A1* | 4/2005 | Toth et al. ......................... 378/16 |
| 2006/0023832 | A1* | 2/2006 | Edic et al. ........................... 378/7 |
| 2011/0243413 | A1* | 10/2011 | Tkaczyk et al. ............... 382/131 |

FOREIGN PATENT DOCUMENTS

JP    2014-004373 A    1/2014

* cited by examiner

*Primary Examiner* — Hoon Song
(74) *Attorney, Agent, or Firm* — Oblon, McClelland, Maier & Neustadt, L.L.P.

(57) ABSTRACT

An apparatus and method for reducing the X-ray flux in a computed-tomography (CT) scanner that includes a rotating X-ray source and a plurality of stationary photon-counting detectors configured to capture incident X-ray photons emitted from the X-ray source. A bowtie filter equipped with an edge filter that can be positioned in a reconfigurable manner such that the high X-ray flux at the leading edge of an X-ray fan beam incident on the detector is reduced. The CT apparatus includes a processor that is configured to compute the displacement of the edge filter in either a static or dynamic manner such that that the intensity of X-ray flux at the detectors in within acceptable operating limits.

18 Claims, 14 Drawing Sheets

APPARATUS AND METHOD FOR REDUCING X-RAY FLUX IN SPECTRAL CT

FIELD

Embodiments disclosed herein generally relate to computed tomography (CT) imaging. In particular, embodiments disclosed herein relate to an apparatus and associated methods for reducing X-ray flux at a leading edge of an X-ray fan beam in spectral CT.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low-energy X-ray from the generator, the details of the geometry and characteristics of the detector, and the capacity of the acquisition system are all elements that affect how the actual reconstruction is performed.

Typical CT systems include an X-ray source and stationary photon-counting detectors (PCDs). The PCDs are configured to acquire spectral data, which is then decomposed into line integrals of the basis material of the imaged object. The basis images of the object can be reconstructed from the line integrals and thus can provide material information of the imaged object. However, the PCDs experience high flux levels during object scanning and may not be able to function correctly. Thus, in order to obtain reliable spectral information of the imaged object, the problem of the high flux in spectral CT apparatus needs to be addressed.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1A:
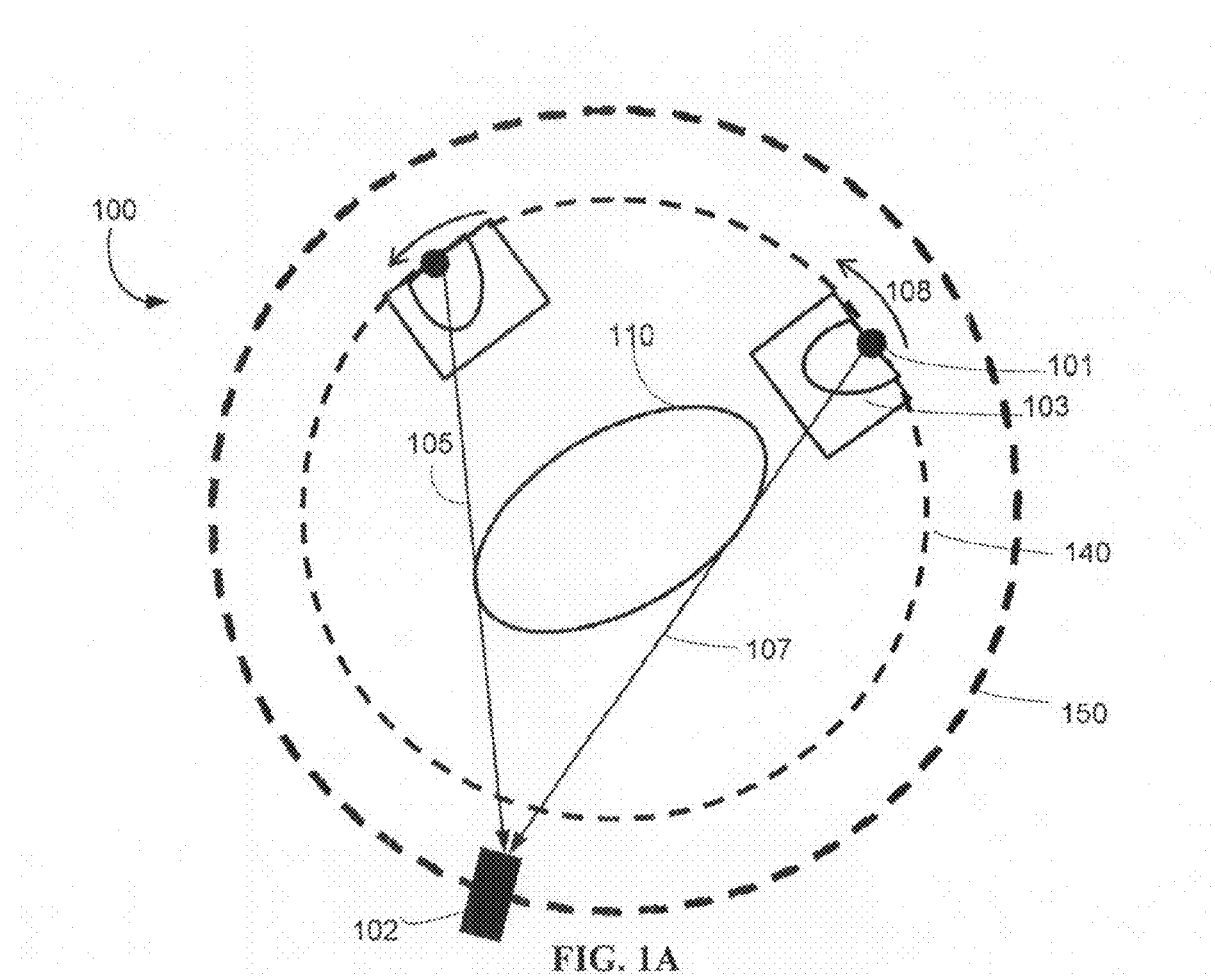
FIG. 1A illustrates a non-limiting example of a CT scanner which includes a bowtie filter and FIG. 1B shows the corresponding X-ray flux experienced by a detector of the CT scanner.

Embodiments disclosed herein relate to an apparatus and corresponding methods for reducing the high X-ray flux of spectral CT.

In one embodiment, there is provided a computed-tomography (CT) apparatus, comprising: a rotating X-ray source; a plurality of stationary photon-counting detectors configured to capture incident X-ray photons emitted from the X-ray source; a bowtie filter, including a movable edge filter, configured to reduce X-ray flux at a leading edge of an X-ray fan beam incident on the photon-counting detector; and a processor configured to obtain a scanogram of an object, compute a voltage and a current value for the X-ray source based on the obtained scanogram, calculate a flux intensity for each photon-counting detector based on the computed voltage and current of the X-ray source, and determine a desired position of the edge filter with respect to the bowtie filter based on the calculated flux intensity.

In another embodiment, there is provided a method for reducing high X-ray flux in a computed-tomography (CT) scanner, the method comprising: obtaining a scanogram of an object; computing a voltage and a current value of an X-ray source of the CT scanner based on the obtained scanogram; calculating a flux intensity for each of a plurality of photon-counting detectors of the CT scanner based on the computed voltage and current values of the X-ray source; determining a desired position of an edge filter with respect to a bowtie filter based on the calculated flux intensity; scanning the object scan based on the determined position of the edge filter; and normalizing the scan of the object with a reference scan.

By another aspect of the disclosure is provided a method for computing a desired position of an edge filter with respect to a bowtie filter, the edge filter being adjacent to and movable with respect to the bowtie filter, the method comprising: defining a maximum flux intensity that a photon-counting detector can sustain; calculating a flux intensity at the photon-counting detector and a ray angle of a leading edge of a X-ray fan beam for each view of a plurality of views of an object based on a scanogram and a computed voltage and current of an X-ray source; computing an attenuation length of the edge filter based on the calculated actual flux intensity; and calculating the desired position of the edge filter with respect to the bowtie filter based on the computed attenuation length.

In another embodiment is provided a non-transitory computer readable medium having stored thereon a program that when executed by a computer, causes the computer to perform the steps of: for reducing high X-ray flux in a computed-tomography (CT) scanner, the method comprising: obtaining a scanogram of an object; computing a voltage and a current value of an X-ray source of the CT scanner based on the obtained scanogram; calculating a flux intensity for a plurality of photon-counting detector of the CT scanner based on the computed voltage and current values of the X-ray source; determining a desired position of an edge filter with respect to a bowtie filter based on the calculated flux intensity; scanning the object scan based on the determined position of the edge filter; and normalizing the scan of the object with a reference scan.

FIG. 1A illustrates a non-limiting example of a CT scanner 100 equipped with a bowtie filter 103. The CT scanner 100 includes an X-ray source 101 that rotates in a circular fashion, along with the bowtie filter 103, around the object to be imaged 110, on the trajectory 140. The X-ray source rotates in the direction indicated by 108, while a stationary detector 102 captures the spectral data of the imaged object. The detector 102 is a semiconductor photon-counting detector such as a CZT detector, CdTe detector, etc. The stationary detector 102 is located along the circular trajectory 150. FIG. 1A shows a leading edge 107 of an X-ray fan beam incident on the detector 102 from a particular position of the X-ray source. Further, as the X-ray source rotates in the direction 108, FIG. 1A also depicts a trailing edge 105 of the X-ray fan beam incident on the detector 102 from another position of the X-ray source.

In CT devices, the X-ray flux experienced by the detector may reach $10^9$ counts per second (cps). Such high count rates prove to be prohibitive for the CZT or the CdTe detectors to function accurately. As an alternative, low dosage techniques such as iterative reconstruction, optimal scan protocol, and low electronic noise technique can be employed. However, the count rates with such techniques could be as high as $10^8$ cps. Current photon-counting detectors such as CZT- or CdTe-based semiconductor detectors are not capable of handling such a high count rate.

The bowtie filter 103 is configured to even the X-ray intensities across the detector array. Although several bowtie filter shapes can be potentially incorporated in a CT scanner to match the different body sizes/shapes of the object 110, the variation of bodies make this choice impractical and results in high flux levels being experienced by the detector 102.

Figure 1B:
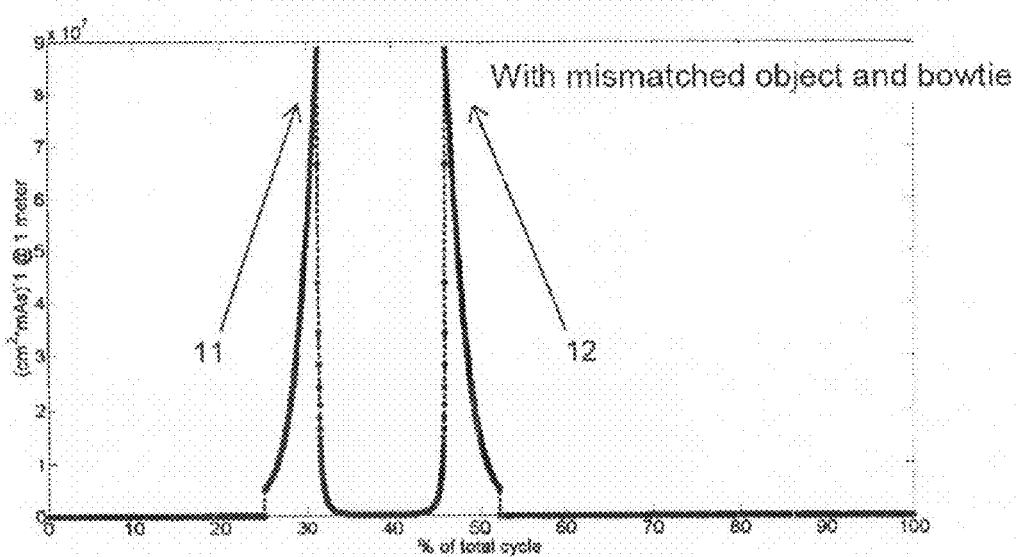

FIG. 1B shows the corresponding X-ray flux experienced by a detector of the CT system of FIG. 1A. Specifically, FIG. 1B shows a plot of the flux experienced by the detector 102 with respect to a duty cycle of the detector 102. There are two peak flux instances experienced by the detector 102. The flux experienced at the leading edge 107 of the X-ray fan beam is shown by 11 in FIG. 1B and the flux experienced by the trailing edge 105 of the X-ray fan beam is shown as 12.

The flux experienced by the detector 102 at the leading edge 107 (represented by 11 in FIG. 1B) occurs at a time instant (as shown in FIG. 1A) when the leading edge impinges the detector. Similarly, the flux experienced by the trailing edge 105 (represented by 12 in FIG. 1B) occurs at a time instance when the X-ray source 101 rotates in the direction represented by 108 and the trailing edge 105 impinges the detector 102. Such a high level of flux is experienced by the detector when the bowtie filter and the object to be imaged are misaligned. After experiencing high flux at the trailing edge of the X-ray fan beam, the detector 102 enters its OFF duty cycle. Thus the detector has sufficient time, corresponding to the amount of time taken by the X-ray source to make a full rotation around a gantry of the scanner and arrive at the detector under consideration, to recover from the state of high flux. However, after experiencing high flux at the leading edge 107 of the X-ray fan beam, the detector enters its ON duty cycle and thus may not have sufficient time to recover from the high flux state. The high flux causes polarization of the semiconductor-based detectors and leads to erroneous detection at the detector.

Figure 2A:
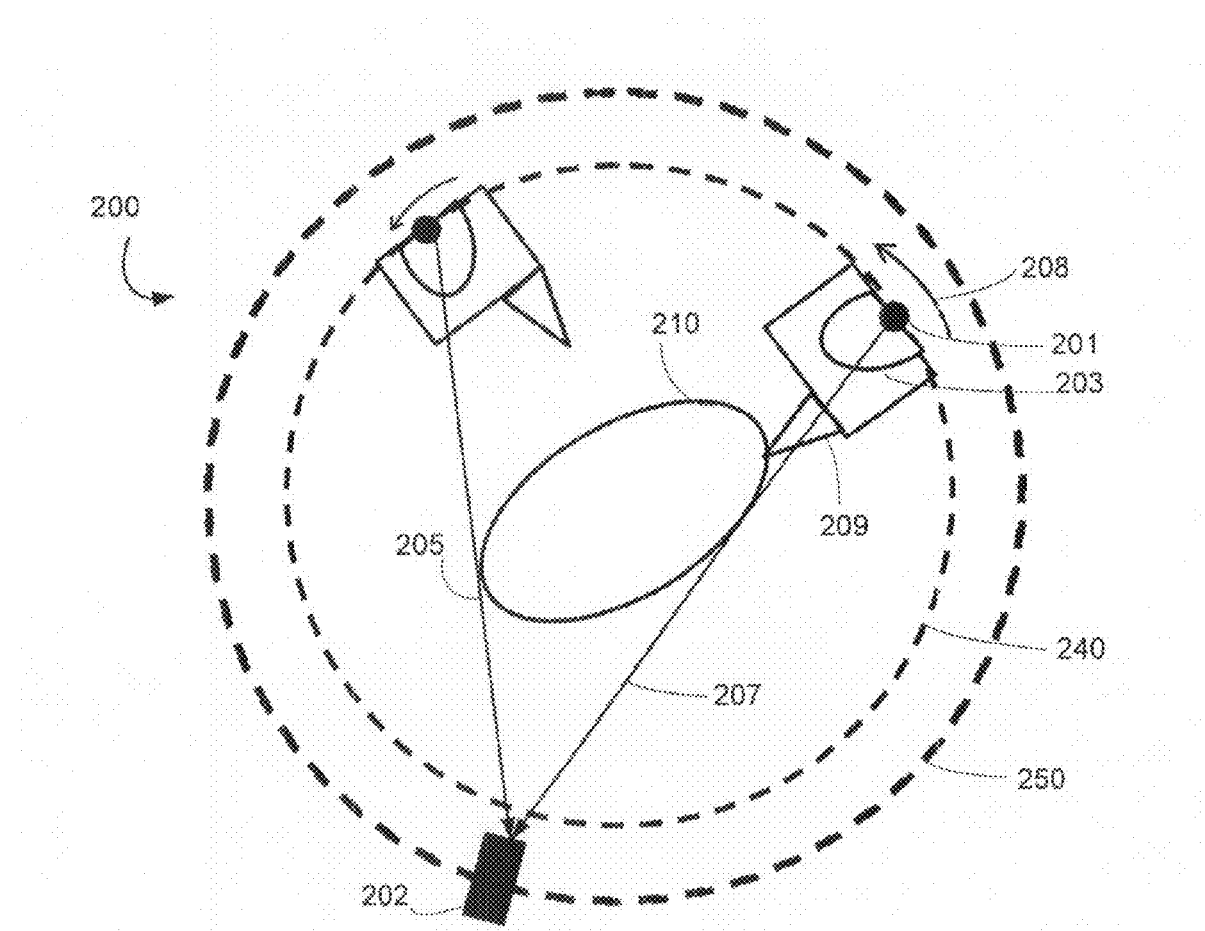
FIG. 2A illustrates a non-limiting example of a CT scanner equipped with an edge filter and FIG. 2B shows the corresponding X-ray flux experienced by a detector of the CT scanner.

FIG. 2A illustrates a non-limiting example of a CT scanner 200 equipped with an edge filter 209. The CT scanner 200 includes an X-ray source 201 and a bowtie filter 203 that rotate in coherence around the object to be imaged 210 on the trajectory 240. The spectral data of the imaged object 210 is captured by stationary detector 202 that is located on the trajectory 250. The X-ray source and the bowtie filter rotate in a direction indicated by 208, in a manner similar to that described in FIG. 1A.

However, to reduce the high level of flux experienced by the detector 202, at the leading edge of the X-ray fan beam 207, the CT scanner 200 includes an edge filter 209 that is disposed on the bowtie filter 203. The combination of the bowtie filter and the edge filter is also referred to as an asymmetric bowtie filter. The shape of the edge filter is such that it can reduce the flux along the leading edge 207 of the X-ray fan beam to a level that the photon-counting detector can handle. Similar to FIG. 1A, FIG. 2A shows a leading edge 207 and a trailing edge 205 incident on the detector 202 from different positions of the X-ray source.

Figure 2B:
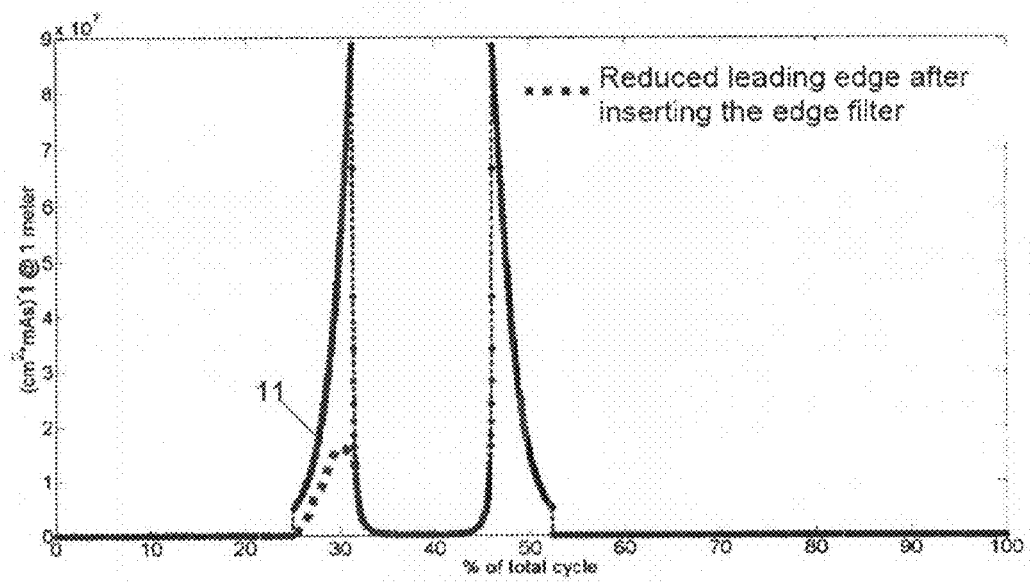

FIG. 2B shows the corresponding X-ray flux experienced by a detector of the CT scanner of FIG. 2A. FIG. 2B shows a plot of the flux experienced by the detector 202 with respect to its duty cycle. By incorporating the edge filter 209, the flux experienced by the detector at the leading edge is reduced to an acceptable level, as shown by the dotted line 11 in FIG. 2B. Specifically, the edge filter reduces the flux at the leading edge to be in the range $1 \times 10^7$ cps to $2 \times 10^7$ cps. Note that the flux experienced by the detector 202 at the leading edge 207 (represented by 11 in FIG. 2B) occurs at a time instant (as shown in FIG. 2A) when the leading edge impinges the detector. Similarly, the flux experienced by the trailing edge 205 (represented by 12 in FIG. 2B) occurs at a time instance when the X-ray source 201 rotates in the direction represented by 208 and the trailing edge 205 impinges the detector 202. Further, note that the edge filter 209 of the CT scanner 200 has a triangular shape. However, this is presented by way of example only, and is not intended to limit the scope of this embodiment. Any other shape of the edge filter that can reduce the flux at the leading edge of the X-ray beam can be used. Further, the X-ray source could be configured to emit either a fan-beam or a cone-shaped X-ray beam.

According to one embodiment, the position of the edge filter on the bowtie filter remains fixed (i.e., stationary) for each captured view. Alternatively, according to another embodiment, the position of the edge filter can be changed in a dynamic manner. Specifically, the position of the edge filter is determined for each captured view. To calculate the stationary and dynamic positions of the edge filter, in order to reduce the flux at the leading edge of the X-ray fan beam, the source (X-ray tube) voltage and current should first be estimated.

The voltage ($V_\lambda$) of the source, expressed in kilo-volts (kV) can be computed by maximizing a dose efficiency (r) and can be represented as $V_\lambda = \mathrm{argmax}\{r\}$. Here $\lambda$ represents the view index of the CT scanner. The dose efficiency is defined as follows:

$$r = \frac{(CNR)^2}{Q}, \qquad (1)$$

where CNR represents a contrast-to-noise ratio in the captured image and Q represents the X-ray radiation dosage. To quantify signals in a region of interest (ROI), the parameter CNR is often implemented. The signal is measured as the mean image intensity in the ROI. The contrast is defined as the difference between the signal in two regions of the ROI. Further, contrast is frequently not a useful parameter in its own right as the scaling factor may be arbitrary. Hence, the contrast is usually normalized to a noise signal.

The radiation dosage Q of equation (1) can be estimated as follows:

$$Q = \sum_{\lambda,j} \int dE E N(E, V_\lambda, A_\lambda) e^{-\mu^{(B)}(E) L_j^{(B)}} (1 - e^{-p_j(E,\lambda)}), \quad (2)$$

where $\lambda$ is the view index and j is the index of the detector. The parameter E represents the energy of a photon and $N(E,V_\lambda, A_\lambda)$ is a photon number of the X-ray source at photon energy E, for tube voltage $V_\lambda$ and current $A_\lambda$. The parameters $\mu^{(B)}(E)$ and $L_j^{(B)}$ are the linear attenuation coefficient and thickness of bowtie filter, respectively. The parameter $p_j(E)$ is a line integral that is obtained by integrating the linear attenuation coefficient $\mu(E, \vec{x})$ along line $l_j$, which is a line determined from the X-ray source to the detector. The line integral can be obtained as:

$$p_j(E, \lambda) = \int_{l_j} dl \mu(E, \vec{x}), \quad (3)$$

Further, the attenuation map can be reconstructed as follows:

$$\mu(E, \vec{x}_i) = \sum_{\lambda,j} R_{i,\lambda,j} p_j(E, \lambda) \quad (4)$$

Here i is the index of image voxel and $(R_{i,\lambda,j})$ is a reconstruction matrix. The image noise is estimated by:

$$\sigma^2(E, \vec{x}_i) = \sum_{\lambda,j} R_{i,\lambda,j}^2 \sigma_j^2(E, \lambda), \quad (5)$$

where $\sigma_j^2(E,\lambda)$ is the variance of the line integral $p_j(E,\lambda)$. Further, ignoring the electronic noise, the data noise can be approximated as:

$$\sigma_j^2(E, \lambda) = \frac{1}{N(E, V_\lambda, A_\lambda) e^{-\mu^{(B)}(E) L_j^{(B)}} e^{-p_j(E,\lambda)}}. \quad (6)$$

Further, the CT images may be contaminated by additive white Gaussian noise. Thus the images may be subject to a denoise process wherein the digital images may be recovered successfully. Assuming that the CT detector has M energy bins and M images are reconstructed, the linear attenuation coefficient at energy E and voxel $i(\mu(E, \vec{x}_i))$, can be expressed as:

$$\mu(E, \vec{x}_i) = \sum_{n=1}^{N} c_n(\vec{x}_i) \mu_n(E), \quad (7)$$

where $\mu_n(E)$ represents a known basis function, for example, the photoelectric probability, Compton probability, linear attenuation coefficients of two basis materials etc.

To denoise an image, a weighted averaging over all the energy bins is performed as:

$$\Sigma_{E=1}^{M} w_{n'E} \mu(E, \vec{x}_i) = \Sigma_{n=1}^{N} c_n(\vec{x}_i) \Sigma_{E=1}^{M} w_{n'E} \mu_n(E) \quad (8)$$

Further, a matrix $m_{\overline{nn}'}$ can be defined as an inverse of the matrix $\Sigma_{E=1}^{M} w_{n'E} \mu_n(E)$, such that the following equation is valid.

$$\Sigma_{E=1}^{M} \Sigma_{n'=1}^{N} m_{\overline{nn}'} w_{n'E} \mu_n(E) = \delta_{\overline{n}n}. \quad (9)$$

Thus, from (7) and (8) we have:

$$\sum_{E=1}^{M} \sum_{n'=1}^{N} m_{\overline{nn}'} w_{n'E} \mu(E, \vec{x}_i) = \sum_{n=1}^{N} c_n(\vec{x}_i) \sum_{E=1}^{M} \sum_{n'=1}^{N} m_{\overline{nn}'} w_{n'E} \mu_n(E) \quad (10)$$

$$\sum_{E=1}^{M} \sum_{n'=1}^{N} m_{\overline{nn}'} w_{n'E} \mu(E, \vec{x}_i) = c_n(\vec{x}_i) \quad (11)$$

Accordingly, the denoised image can be expressed as, $$\overline{\mu}(E, \vec{x}_i) = \Sigma_{n=1}^{N} \Sigma_{E'=1}^{M} \Sigma_{n'=1}^{N} m_{nn'} w_{n'E} \mu(E', \vec{x}_i) \mu_n(E). \quad (12)$$

To further simplify the above equations, we define:

$$W(E,E') = \Sigma_{n=1}^{N} \Sigma_{n'=1}^{N} m_{nn'} w_{n'E} \mu_n(E) \quad (13)$$

From (13), the standard deviation of the denoised image can be expressed as:

$$\overline{\sigma}^2(E, \vec{x}_i) = \sum_{E'=1}^{M} W^2(E, E') \sigma^2(E', \vec{x}_i). \quad (14)$$

wherein the optimal weights can be determined by $$w_{nE} = \mathrm{argmin}\left\{\sum_{E'=1}^{M} W^2(E, E') \sigma^2(E', \vec{x}_i)\right\}, \quad (15)$$

subject to $$\sum_{E=1}^{M} w_{n'E} = 1. \quad (16)$$

For an imaging task where the attenuation coefficients of the contrast and the background are $\mu_C(E)$ and $\mu_B(E)$ respectively, the contrast-to-noise ratio can be expressed as:

$$(CNR)^2 = \frac{(\mu_C(E) - \mu_B(E))^2}{\overline{\sigma}^2(E, \vec{x}_{i_B})}, \quad (17)$$

where $i_B$ indicates an image voxel in the background. Upon substituting equation (6) into equation (17), the contrast-to-noise ratio can be computed as shown below;

$$(CNR)^2 = \frac{(\mu_C(E) - \mu_B(E))^2}{\sum_{E'=1}^{M} \sum_{\lambda,j} \frac{W^2(E, E')R_{i_B,\lambda,j}^2}{N(E', V_\lambda, A_\lambda)e^{-\mu^{(B)}(E)L_j^{(B)} - p_j(E',\lambda)}}} \quad (18)$$

Once the contrast-to-noise ratio is computed as shown in equation (18), the dose efficiency of (1) can computed by a simple substitution of equation (18) into equation (1). Hence the dose efficiency can be represented as:

$$r = \frac{(\mu_C(E) - \mu_B(E))^2}{\sum_{E'=1}^{M} \sum_{\lambda,j} \frac{W^2(E, E')R_{i_B,\lambda,j}^2}{N(E', V_\lambda, A_\lambda)e^{-\mu^{(B)}(E)L_j^{(B)} - p_j(E',\lambda)}}} \cdot \frac{1}{\sum_{\lambda,j} \int dE E N(E, V_\lambda, A_\lambda) e^{-\mu^{(B)}(E)L_j^{(B)}}(1 - e^{-p_j(E,\lambda)})} \quad (19)$$

Accordingly, the tube voltage $V_\lambda$ is computed as a maximum of the function represented by (19). Further, consider a single view $\lambda$ of the CT system, and a monochromatic source. The dose efficiency of this single view $r(\lambda)$ can be expressed as follows:

$$r(\lambda) = \frac{(\mu_C(E) - \mu_B(E))^2 e^{-\overline{p}(E,\lambda)}}{E(1 - e^{-\overline{p}(E,\lambda)})} \quad (20)$$

The average line integral $$\overline{p}(E, \lambda) = \sum_{j=1}^{j} \frac{1}{j} p_j(E, \lambda)$$

can be estimated from the acquired views. The optimal energy at a particular view index $E(\lambda)$ can then be represented as:

$$E(\lambda) = \mathrm{argmax}\{r(\lambda)\} = \mathrm{argmax}\left\{\frac{(\mu_C(E) - \mu_B(E))^2 e^{-\overline{p}(E,\lambda)}}{E(1 - e^{-\overline{p}(E,\lambda)})}\right\} \quad (21)$$

The optimal energy can be related to tube voltage $V_\lambda$ by, $$E(\lambda) = \frac{\sum_j \int dE E N(E, V_\lambda, A_\lambda) e^{-\mu^{(B)}(E)L_j^{(B)}}}{\sum_j \int dE N(E, V_\lambda, A_\lambda) e^{-\mu^{(B)}(E)L_j^{(B)}}} \quad (22)$$

By using voltage modulation, the tube voltage can be set according to $V_\lambda$. Without voltage modulation, the tube voltage can simply be set as:

$$V = \frac{1}{N_{view}} \sum_{\lambda=1}^{N_{view}} V_\lambda \quad (23)$$

Further, assuming that each acquired view (scanogram) of the imaged object has the same noise level, the product of the tube current and the dose efficiency of the view is constant. Specifically, $A_\lambda r(\lambda)$=Const. Hence, the tube current $A_\lambda$ can be acquired by substituting the value of $r(\lambda)$ that is computed using equation (20) as shown below:

$$A_\lambda = \mathrm{Const} \frac{E(1 - e^{-\overline{p}(E,\lambda)})}{(\mu_C(E) - \mu_B(E))^2 e^{-\overline{p}(E,\lambda)}}. \quad (24)$$

Once the voltage and current of the source are determined as described above, the position of the edge filter that is displaced on the bowtie filter is computed. The parameters governing the position of the edge filter are the count rate (flux) observed by a detector at a given position on the bowtie filter and an additional attenuation length required to maintain an acceptable flux level experienced by the detector. The edge filter should be placed so that the flux experienced by the detector is within acceptable limits. In order to compute the position of the edge filter, a count rate that corresponds to the flux experienced by the detector is estimated. The count rate can be defined as the total counts obtained from all the energy bins of the detector. The count rate n(λ,j) can be computed based on the voltage and current parameters already computed, as follows:

$$n(\lambda, j) = \int dE N(E, V_\lambda, A_\lambda) e^{-\mu^{(B)}(E)L_j^{(B)} - \mu^{(a)}(E)L_j^{(a)}(x) - p_j(E,\lambda)} \quad (25)$$

The stationary position of the edge filter, according to an embodiment of the disclosure is computed such that $n(\lambda,j) < n_{max}$, where $n_{max}$ is a known maximum count rate (flux) that the PCD detector can sustain. Alternatively, for another embodiment, which computes the positions of the edge filter in a dynamic manner, the position $x(\lambda)$ for each view can be computed such that $n(\lambda,j) < n_{max}$, where the count rate for each view can be computed as $$n(\lambda, j) = \int dE N(E, V_\lambda, A_\lambda) e^{-\mu^{(B)}(E)L_j^{(B)} - \mu^{(a)}(E)L_j^{(a)}(x(\lambda)) - p_j(E,\lambda)} \quad (26)$$

Figure 3:
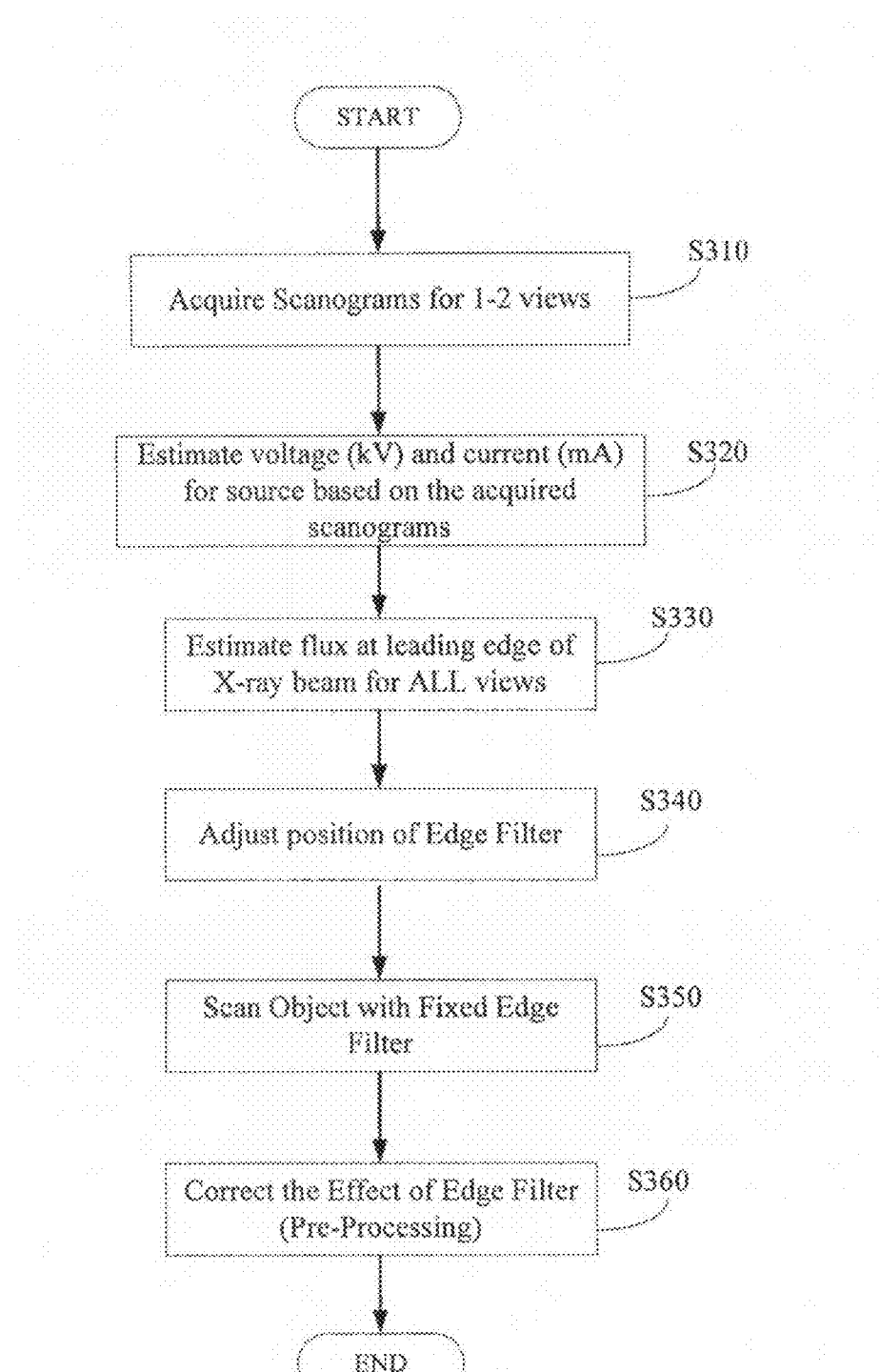
FIG. 3 is a flowchart illustrating the steps performed for reducing the X-ray flux by using a stationary edge filter.

FIG. 3 is a flowchart illustrating the steps performed for reducing the X-ray flux by using a stationary edge filter.

In step S310, the CT scanner acquires one or more scanograms (views) of the imaged object.

In step S320, based on the acquired scanograms, the source voltage and current are determined as described above. Specifically, by using equations (22)-(24) the voltage and current of the X-ray tube (source) is determined.

In step S330, the flux at the leading edge of the X-ray fan beam is determined for all the views using equation (25). Further, based on the flux computed for all the views, an additional attenuation length (L) of the edge filter is determined, such that the flux experienced by the detector is less than a maximum flux threshold that the detector can handle.

Figure 4:
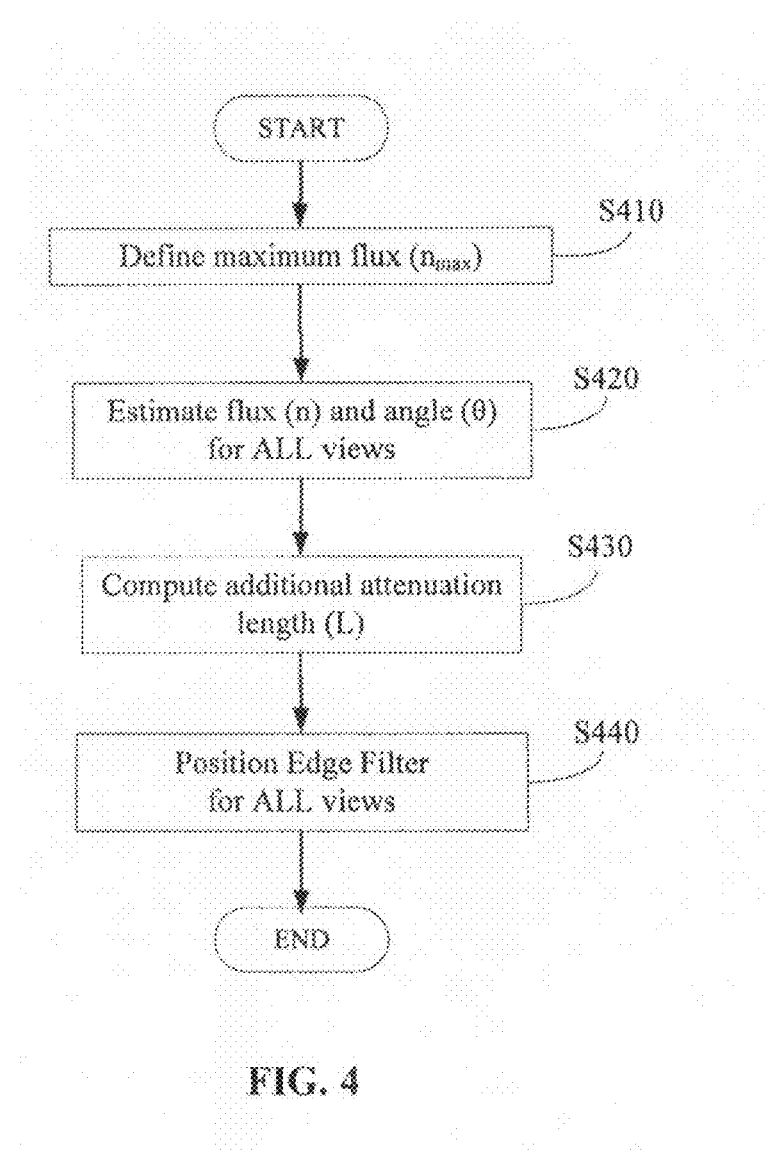
FIG. 4 is a flowchart illustrating the steps performed in determining the static position of the edge filter.

The computation of the required attenuation length (L) is determined using the process shown in FIG. 4.

In step S340, upon computing the flux and the required attenuation length, the edge filter is positioned.

In step S350, the object is scanned with the edge filter positioned at a fixed location along the edge of the bowtie filter for all views.

In step S360, a pre-processing is performed on the view data obtained by scanning the object in step S350. The pre-processing operation on the object scan is achieved by normalizing the object scan with a reference scan (for example a reference scan of an air or water phantom of known dimension, etc). The pre-processing operation is a logarithmic operation that can be represented as:

$$I_{j,\lambda} = \log \frac{I_{ref,j,\lambda}}{I_{obj,j,\lambda}} \quad (27)$$

where the index j represents the photon-counting detector index, and the index λ represents the view index. The pre-processed scanned view $I_{j,\lambda}$ is input to reconstruct the imaged object.

FIG. 4 is a flowchart illustrating the steps performed in computing the attenuation length and the static position of the edge filter.

In step S410, the maximum flux threshold $n_{max}$ that the photon-counting detector can handle is defined. This threshold sets an upper limit for the flux that can be experienced at each view of the CT system. A flux level higher than $n_{max}$ may render the detector ineffective. The maximum flux that a detector can handle is independent of the X-ray source and the object that is to be scanned. The maximum flux is an intrinsic detector property.

In step S420, the flux experienced by the detector for all the views is computed by equation (25). Further, an angle theta (θ) that the leading edge of the X-ray fan beam makes with a reference X-ray beam is determined. The reference X-ray beam is the beam that originates from the X-ray source and traverses through the center of the bowtie filter. The reference beam is oriented perpendicular to an edge of the bowtie filter.

In step S430, the additional attenuation length (L) of the edge filter required in order to ensure that the flux experienced by the detector is less than the maximum threshold flux is determined. The length (L) can be computed such that the following constraint is satisfied:

$$L \geq \frac{\log(n/n_{max})}{\tilde{\mu}} \quad (28)$$

where $\tilde{\mu}$ is the average linear attenuation of the filter and n is the maximum count rate measured without the edge filter for all views λ, and all detectors j.

In step S340, the edge filter is positioned along the edge of the bowtie filter for all views based on the computed additional attenuation length of step S430. The positioning of the edge filter in step S440 is described with respect to FIG. 5.

Figure 5:
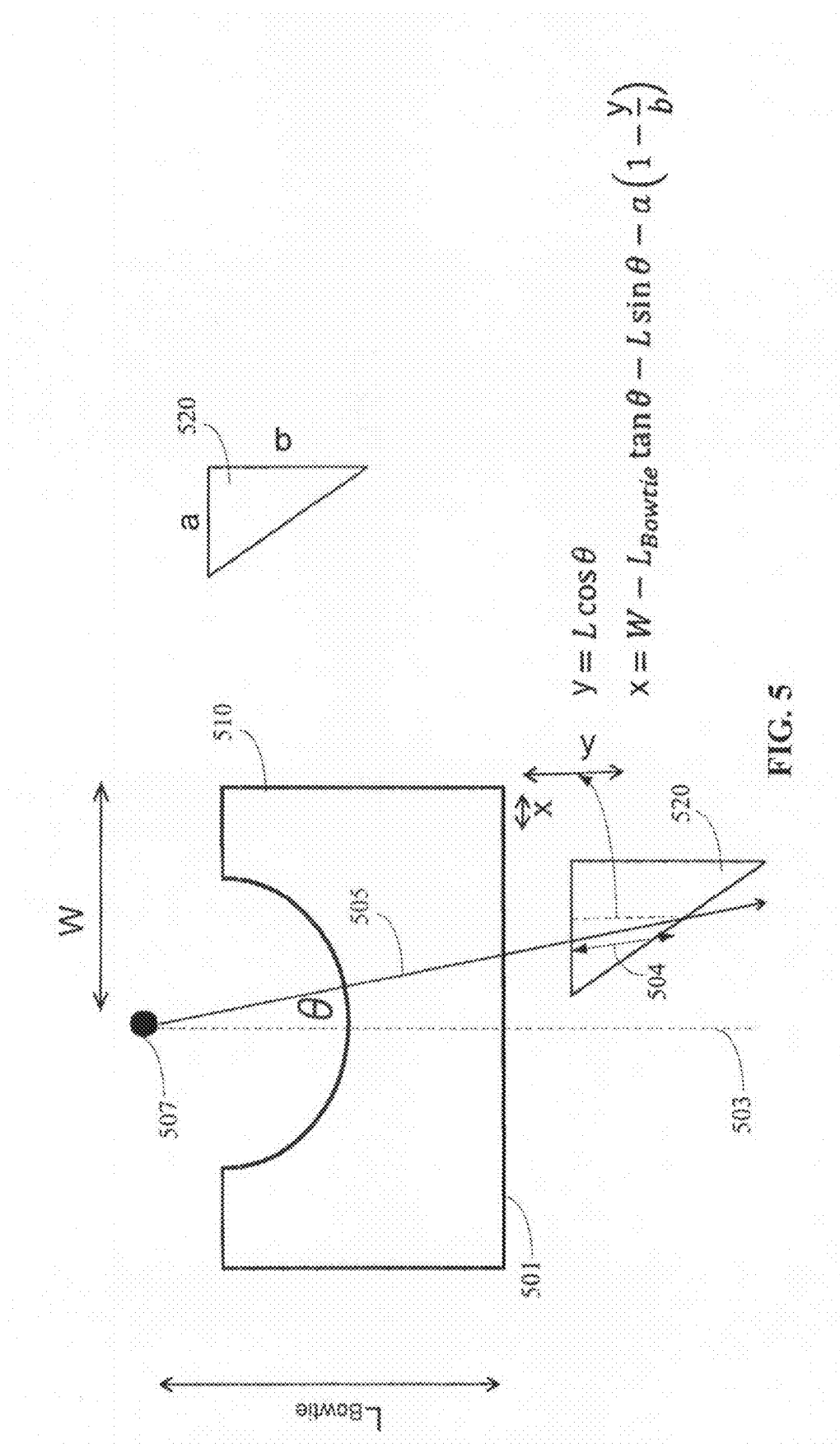
FIG. 5 shows a non-limiting example illustrating the attenuation length required for statically positioning the edge filter.

FIG. 5 shows a non-limiting example depicting the additional attenuation length (L), and the corresponding computations performed to determine the position of the edge filter. The edge filter shown in FIG. 5 has the shape of a right-angled triangle. This is presented by way of example only, and is not intended to limit the scope of the disclosed embodiments.

Other shapes of edge filter that satisfy the maximum flux and attenuation length constraints described above can also be used.

FIG. 5 shows a bowtie filter 510 with edges of dimensions $L_{bowtie}$ and 2 W respectively. The X-ray source 507 forms a leading edge 505 and a reference edge 503. The angle formed between the leading edge 505 and the reference edge 503 is θ. The edge filter 520 has a right-angled triangular shape, with edges of length 'a' and 'b' respectively. The length represented by 504 of the edge filter is the additional attenuation length required to ensure that the flux experienced by the detector is lower than the maximum threshold flux the detector can handle. Further, the edge filter is shown separated from the bowtie filter for sake of illustration. In practice the edge filter is disposed on the edge 501 of the bowtie filter 510. The position of the edge filter 520, along the edge 501 of the bowtie filter can be computed as a displacement 'x' from the edge of the bowtie filter. The displacement x, can be computed as:

$$x = W - L_{bowtie} \tan\theta - L\sin\theta - a\left(1 - \frac{y}{b}\right), \quad (29)$$

where $y = L\cos\theta$

Based on above computed displacement, the edge filter 520 is positioned accordingly for the views of the CT system and reduces the flux experienced by the detector at the leading edge of the X-ray beam.

Figure 6:
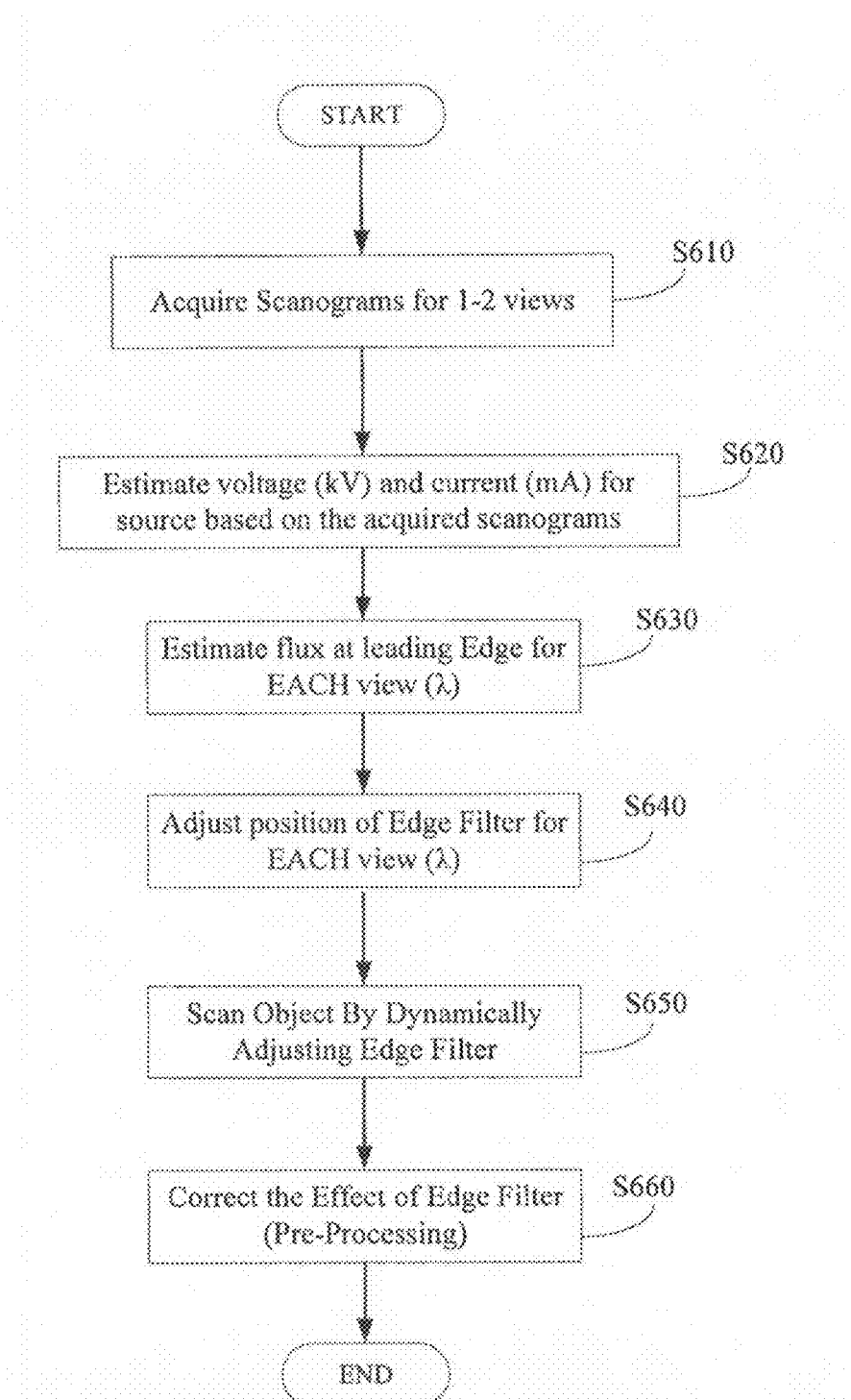
FIG. 6 is a flowchart illustrating the steps performed for reducing the X-ray flux by using a dynamic edge filter.

FIG. 6 is a flowchart illustrating the steps performed for reducing the X-ray flux at the leading edge of the X-ray fan beam by changing the position of the edge filter dynamically for each view.

Steps S610 and S620 of the flowchart shown in FIG. 6 are similar to steps S310 and S320 of the stationary edge filter described in FIG. 3.

However, in step S630, the flux experienced by the detector is computed at each view by using equation (26). Once the flux is computed for each view, an additional attenuation length for each view $L_\lambda$ of the edge filter is determined, such that the flux experienced by the detector is less than a maximum flux threshold that the detector can handle. The computation of the required attenuation length $L_\lambda$ is described with respect to FIG. 7.

In step S640, upon computing the flux and the required attenuation length for each view, the edge filter is positioned accordingly at each view.

In step S650, the object is scanned with the edge filter being dynamically positioned for each view.

In step S660, a pre-processing is performed on the view data obtained by scanning the object in step S650. The pre-processing operation is similar to the logarithmic operation performed for the stationary edge filter.

Figure 7:
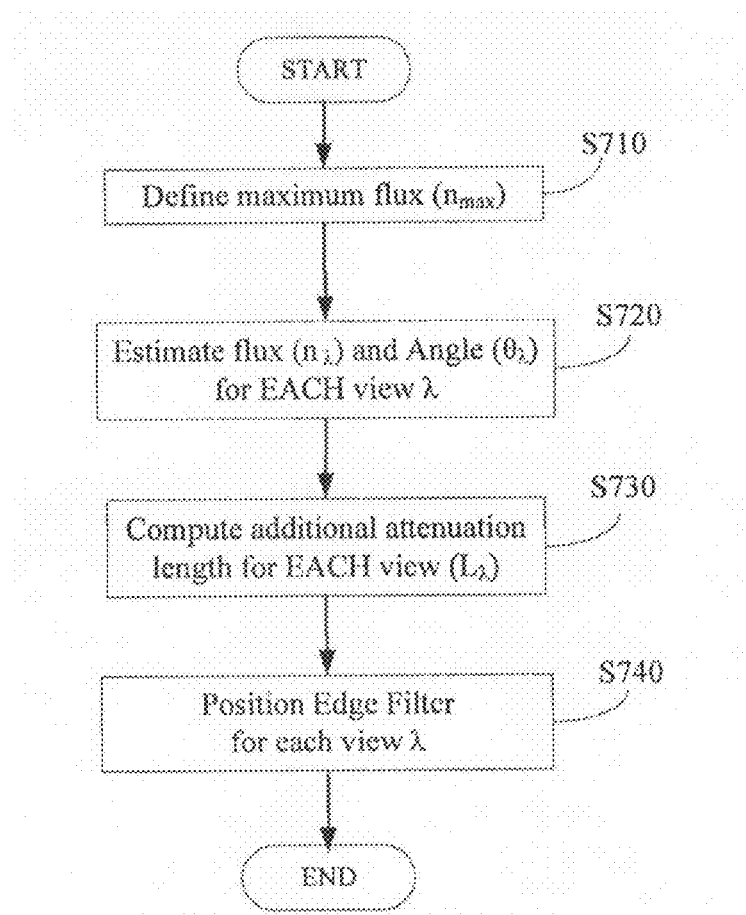
FIG. 7 is a flowchart illustrating the steps performed to determine the dynamic position of the edge filter.

FIG. 7 is a flowchart illustrating the steps performed in computing the position of the edge filter for each view in the dynamic case. In this embodiment, a controller may be configured to adjust the position of the edge filter, along the edge of the bowtie filter, at each of the computed displacements.

In step S710, the maximum flux threshold $n_{max}$ that the photon-counting detector can handle is defined. As stated before, this threshold sets an upper limit for the flux that can be experienced at each view of the CT system. A flux level higher than $n_{max}$ may render the detector ineffective.

In step S720, the flux experienced by the detector for each view is computed by equation (26). Further, an angle $\theta_\lambda$ that the leading edge of the X-ray beam makes with a reference X-ray beam is determined for each view.

In step S730, the additional attenuation length ($L_\lambda$) that the edge filter needs to provide to ensure that the flux experienced by the detector is less than the maximum threshold flux is determined for each view. The length ($L_\lambda$) can be computed such that the following constraint is satisfied:

$$L_\lambda \geq \frac{\log(n_\lambda / n_{max})}{\tilde{\mu}} \quad (30)$$

where $\tilde{\mu}$ is the average linear attenuation of the filter and $n_\lambda$ is the maximum count rate measured without the edge filter, of all the detectors j, for a given view $\lambda$.

In step S740, on computing the additional attenuation length for each view in step S730, the edge filter is positioned along the edge of the bowtie filter for all views. The positioning of the edge filter for each view in step S740 is described with respect to FIG. 8.

Figure 8:
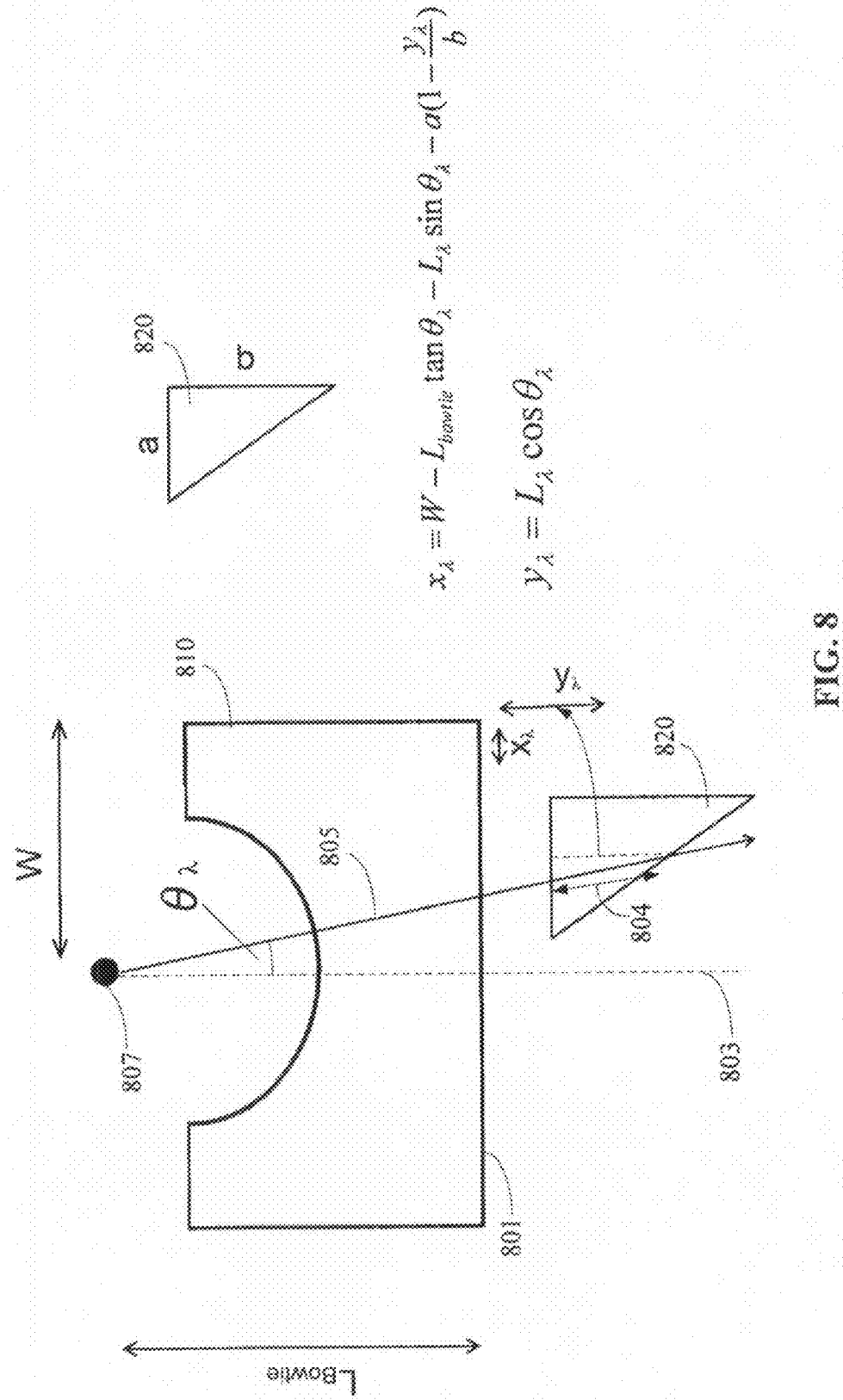
FIG. 8 shows a non-limiting example illustrating the attenuation length required for dynamically positioning the edge filter.

FIG. 8, shows according to one embodiment, a bowtie filter 810 with edges of dimensions $L_{bowtie}$ and 2 W respectively. The X-ray source 807 forms a leading edge 805 and a reference edge 803. The angle (for each view) formed between the leading edge 805 and the reference edge 803 is theta ($\theta_\lambda$). Similar to the example shown in FIG. 5, the edge filter 820 of the present embodiment has a right-angled triangular shape with edges of length 'a' and 'b' respectively. The length represented by 804 of the edge filter is the additional attenuation length required for view $\lambda$ to ensure that the flux experienced by the detector is lower than the maximum threshold flux the detector can handle.

The position of the edge filter 820 for view $\lambda$, along the edge 501 of the bowtie filter, can be computed as a displacement '$x_\lambda$' from the edge of the bowtie filter. The displacement $x_\lambda$, can be computed as:

$$x_\lambda = W - L_{bowtie}\tan\theta_\lambda - L_\lambda \sin\theta_\lambda - a\left(1 - \frac{y_\lambda}{b}\right), \quad (31)$$

where $y_\lambda = L_\lambda \cos\theta_\lambda$

Based on above computed displacement, the edge filter 820 is positioned accordingly for each of the view of the CT system in order to reduce the flux experienced by the detector at the leading edge of the X-ray fan beam for each respective view.

Figure 9:
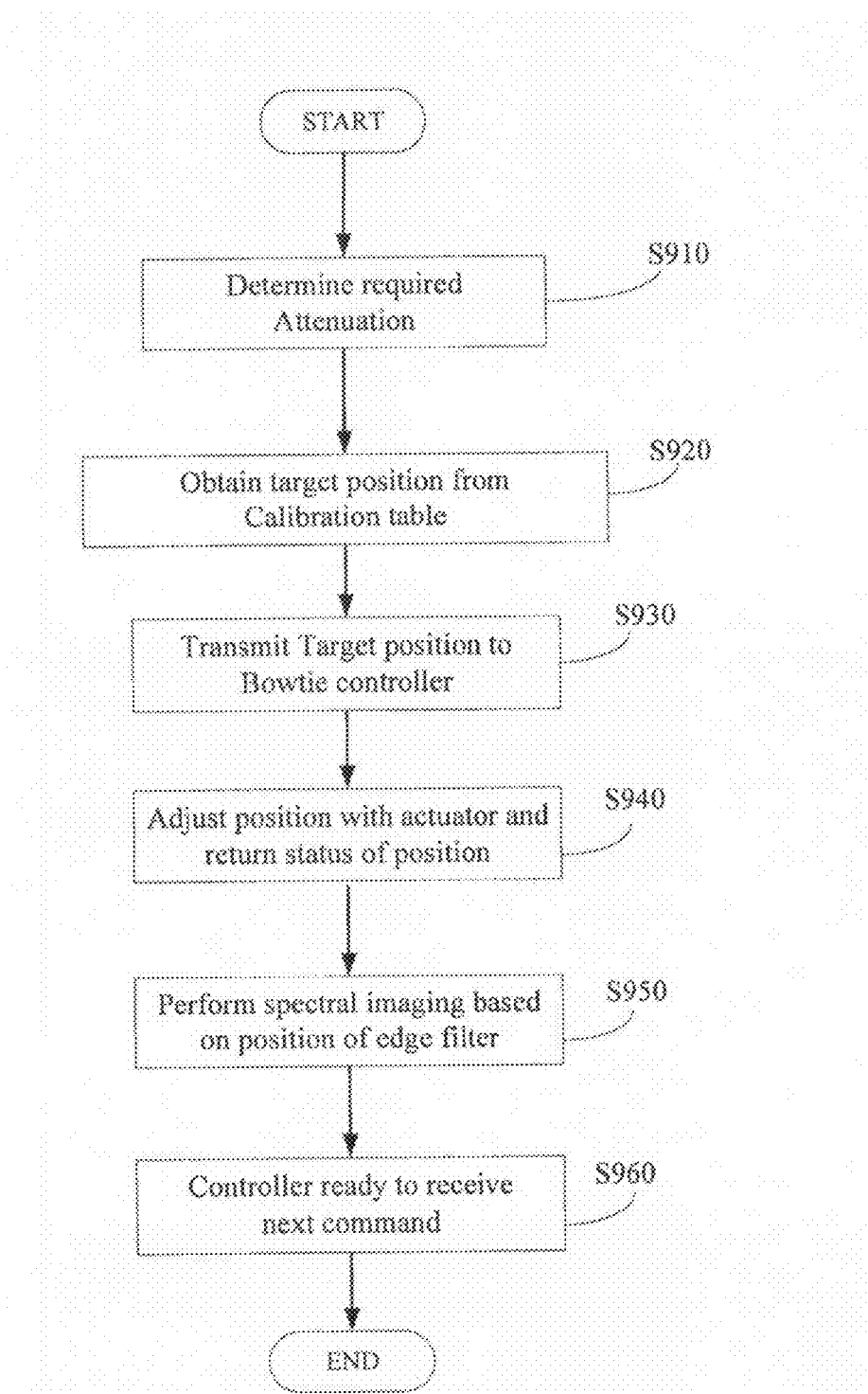
FIG. 9 is an exemplary asymmetric bowtie filter positioning process.

FIG. 9 is an exemplary asymmetric bowtie filter positioning process. Specifically, the flowchart of FIG. 9 illustrates the steps performed by a controller of the CT system in positioning the edge filter.

The combination of the bowtie filter and the edge filter is also referred to as an asymmetric bowtie filter assembly. The bowtie filter assembly includes an electromechanical device, such as a stepper motor, etc. that is configured to accurately position the edge filter along an edge of the bowtie filter. Further, the bowtie filter assembly may also include a positioning sensor that reports the actual position of the edge filter to a bowtie controller. The bowtie filter may also be configured to receive external commands to move the edge filter to a desired position. Furthermore, the CT system also maintains a calibration table that includes a relationship between the position of the edge filter and the corresponding attenuation.

The process begins at step S910, where a controller of the CT system determines the required attenuation length (L) as described with respect to FIG. 4. In step S920 the controller queries a calibration table to obtain a position (displacement along the edge of the bowtie filter) corresponding to the determined attenuation length.

In step S930, the target position that corresponds to the attenuation length is transmitted to a bowtie controller. In step S940, the bowtie controller activates an actuator that positions the edge filter at the desired position along the bowtie filter. Further, the bowtie controller may sense the position of the edge filter via a position scanner and report the position of the edge filter to the CT system controller.

In step 950, the CT apparatus performs spectral imaging of the object with the computed position of the edge filter.

According to one embodiment, a method may be implemented for statically positioning the edge filter along the edge of the bowtie filter. In such a method, the position of the edge filter, once computed, remains constant for all successive views until the controller initiates a re-computation, on receiving a command as shown in step S960. Alternatively, the method can also be used to adjust the position of the edge filter along the edge of the bowtie filter in a dynamic manner. In such a method, the bowtie controller is configured to accurately position the edge filter at each view of the CT system.

Figure 10:
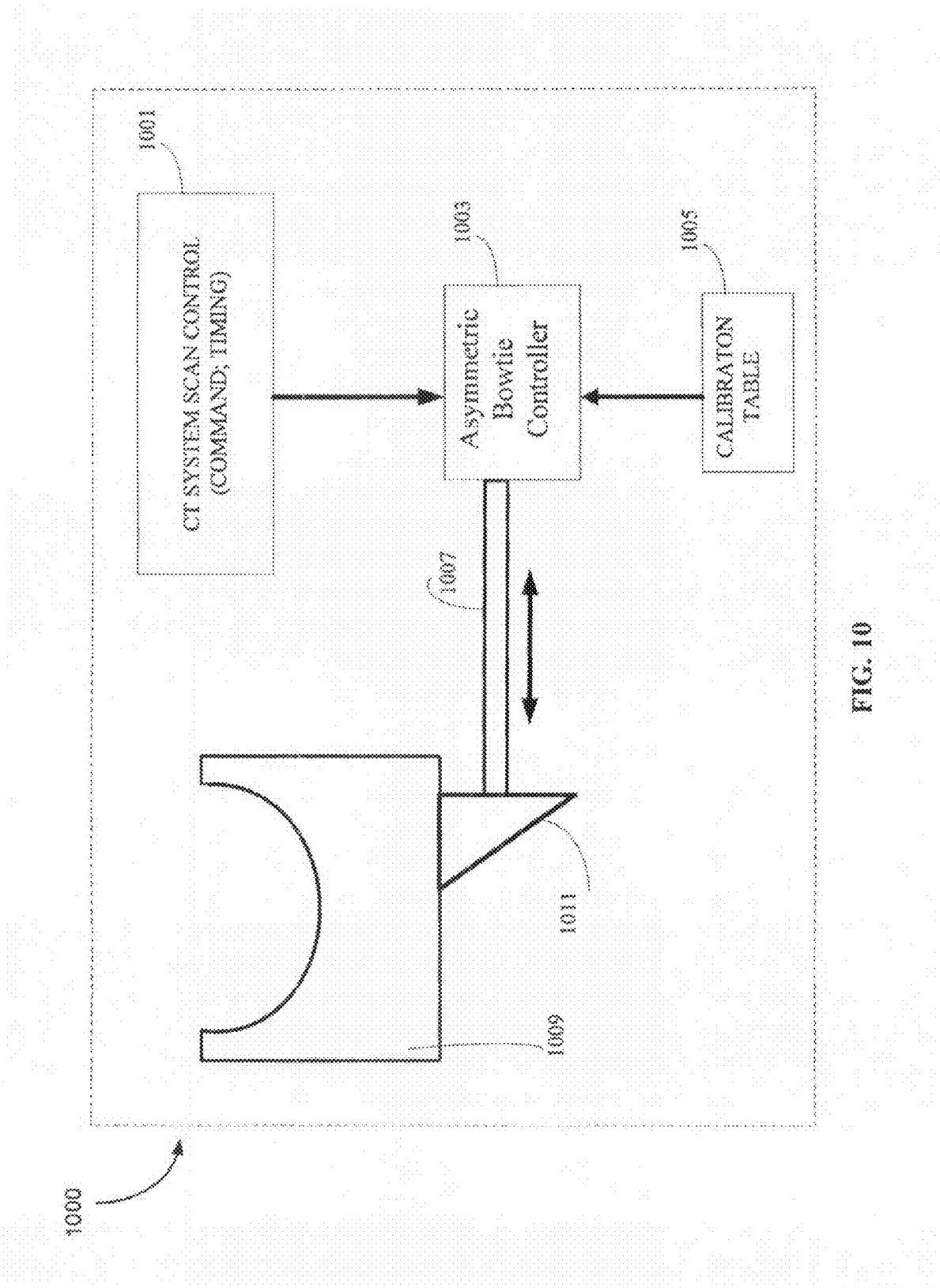
FIG. 10 shows a non-limiting example of a CT system according to one embodiment of the disclosure illustrating the static control of the asymmetric bowtie filter.

FIG. 10 shows a non-limiting example of a CT system 1000 according to one embodiment illustrating the static control of the asymmetric bowtie filter.

The bowtie filter 1009 includes a right-angled triangular shaped edge filter 1011. The CT system controller 1001 is configured to transmit command instructions and timing signals to the asymmetric bowtie controller 1003. The bowtie controller 1003 controls an actuator 1007, such as a stepper motor, etc. to control the position of the edge filter 1011 that is disposed on the edge of the bowtie filter 1009.

As described with respect to FIG. 9, the CT controller can determine the attenuation length required by the edge filter in order to keep the flux at the leading edge of the X-ray beam within permissible limits. The CT controller 1001 transmits the required attenuation length to the bowtie controller 1003, which queries a calibration table 1005, such as a look-up table or the like to find the corresponding position of the edge filter 1011.

Upon acquiring the desired position, the bowtie controller 1003 activates the actuator 1007 to displace the edge filter 1011 at the desired position.

Figure 11:
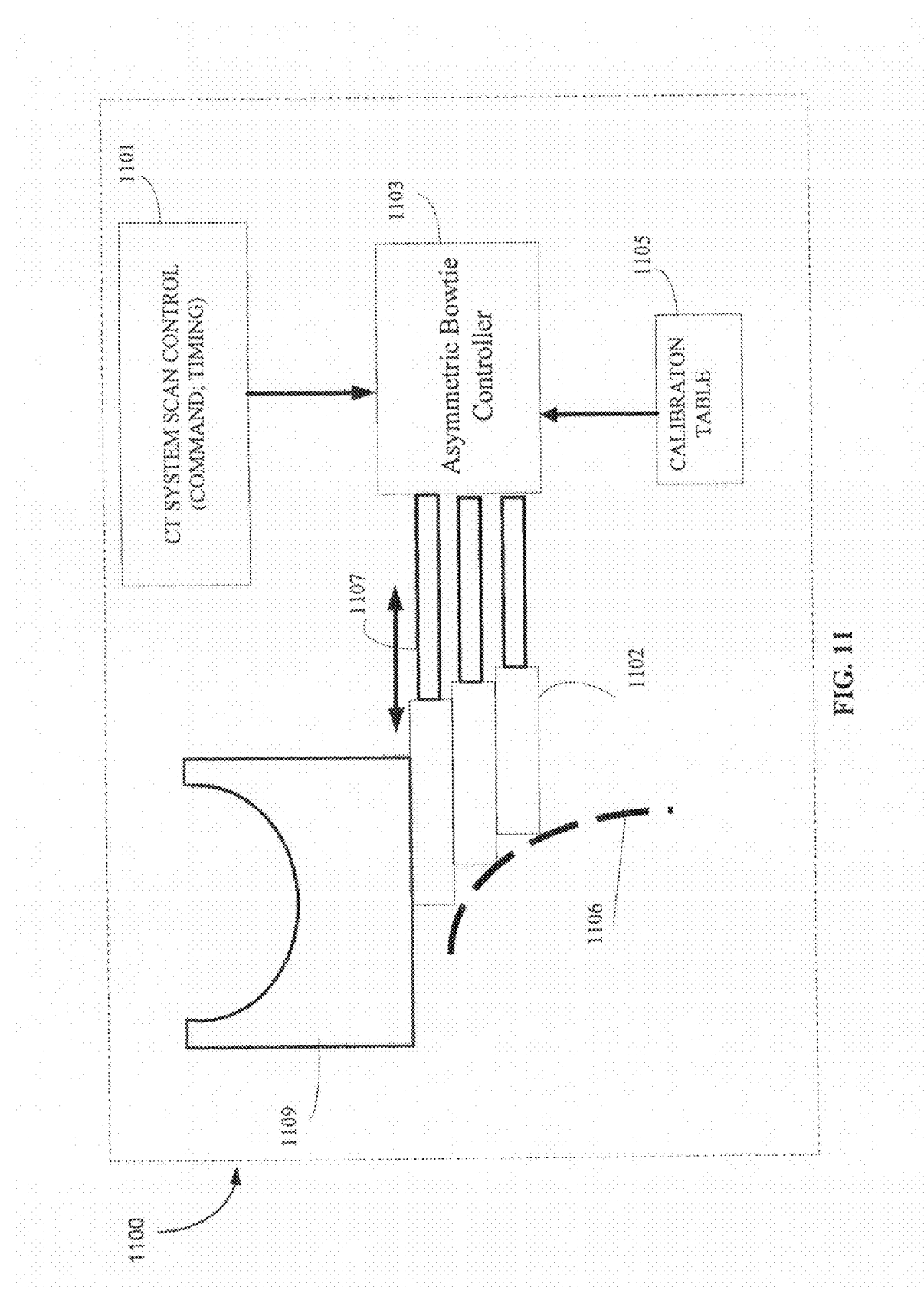
FIG. 11 shows a CT system according to another embodiment of the disclosure implementing the dynamic control of the asymmetric bowtie filter.

FIG. 11 shows a CT system 1100 according to another embodiment implementing the dynamic control of the asymmetric bowtie filter. Specifically, the CT system controller 1101, the bowtie controller 1103, and the calibration table 1105 are configured in a manner similar to that of FIG. 10. However, the bowtie controller 1103 is further configured to change the position of the edge filter 1109, via the actuator 1107, for each view of the CT system. Thus, an edge profile 1106 of the edge filter 1102 can be varied based on the size and shape of the object to be imaged.

Figure 12:
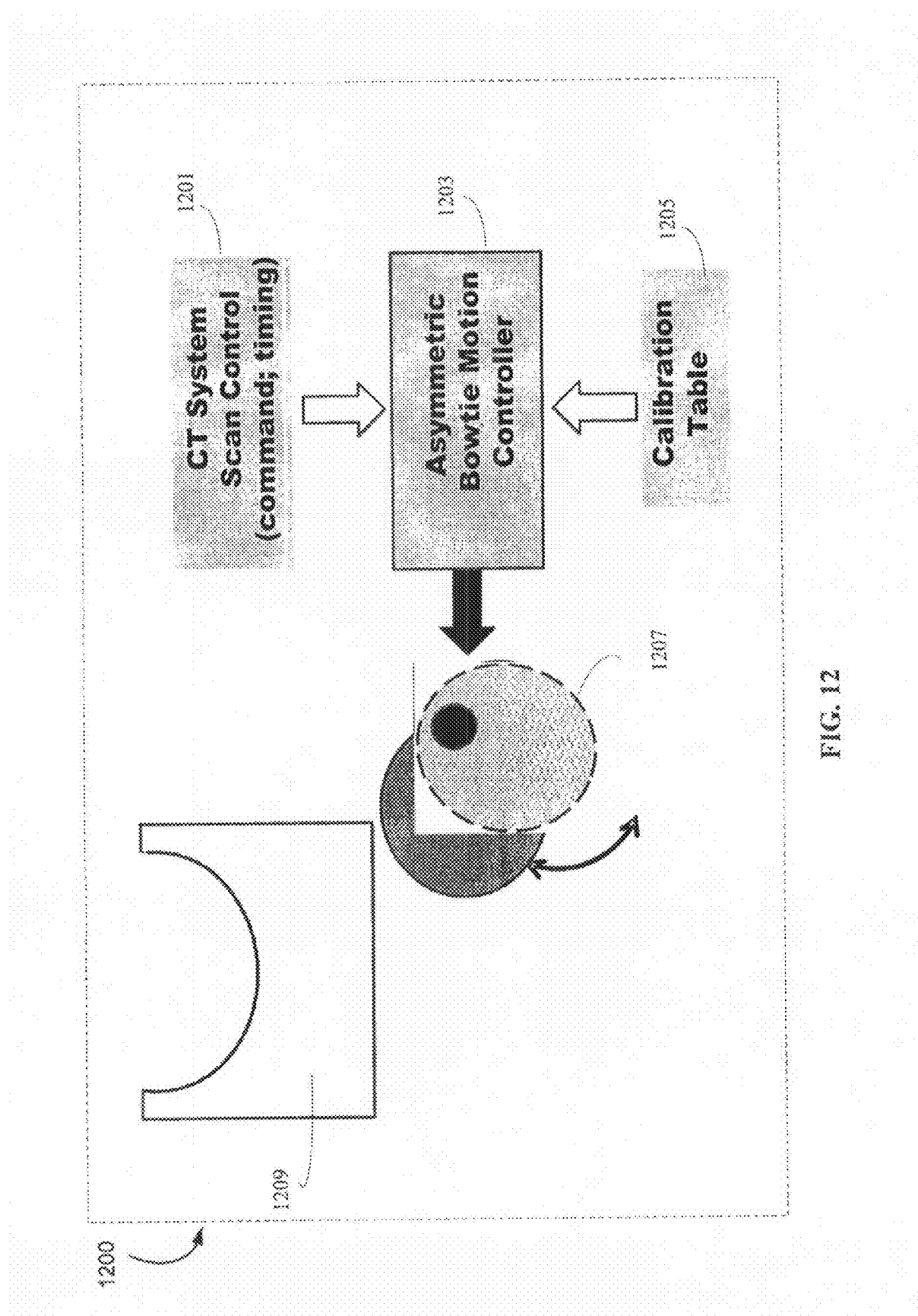
FIG. 12 shows a CT system according to another embodiment controlling a circularly shaped edge filter.

FIG. 12 shows a CT system 1200 according to another embodiment of the disclosure implementing dynamic control of the asymmetric bowtie filter. The CT controller 1201, the asymmetric bowtie controller 1203, and the calibration table 1205 are configured in a similar manner to that described with reference to FIG. 11.

However, the CT system 1200 includes a circular-shaped edge filter 1207. An actuator such as a rotary motor can be used to displace the edge filter 1207 along the edge of the bowtie filter 1209. Using a circular-shaped edge filter 1209 provides the advantage of rapidly changing the attenuation of the asymmetric bowtie filter. This is particularly useful in situations where the rotational speeds of the X-ray source may be high and where a quick change of attenuation is required from one view to the next.

Figure 13:
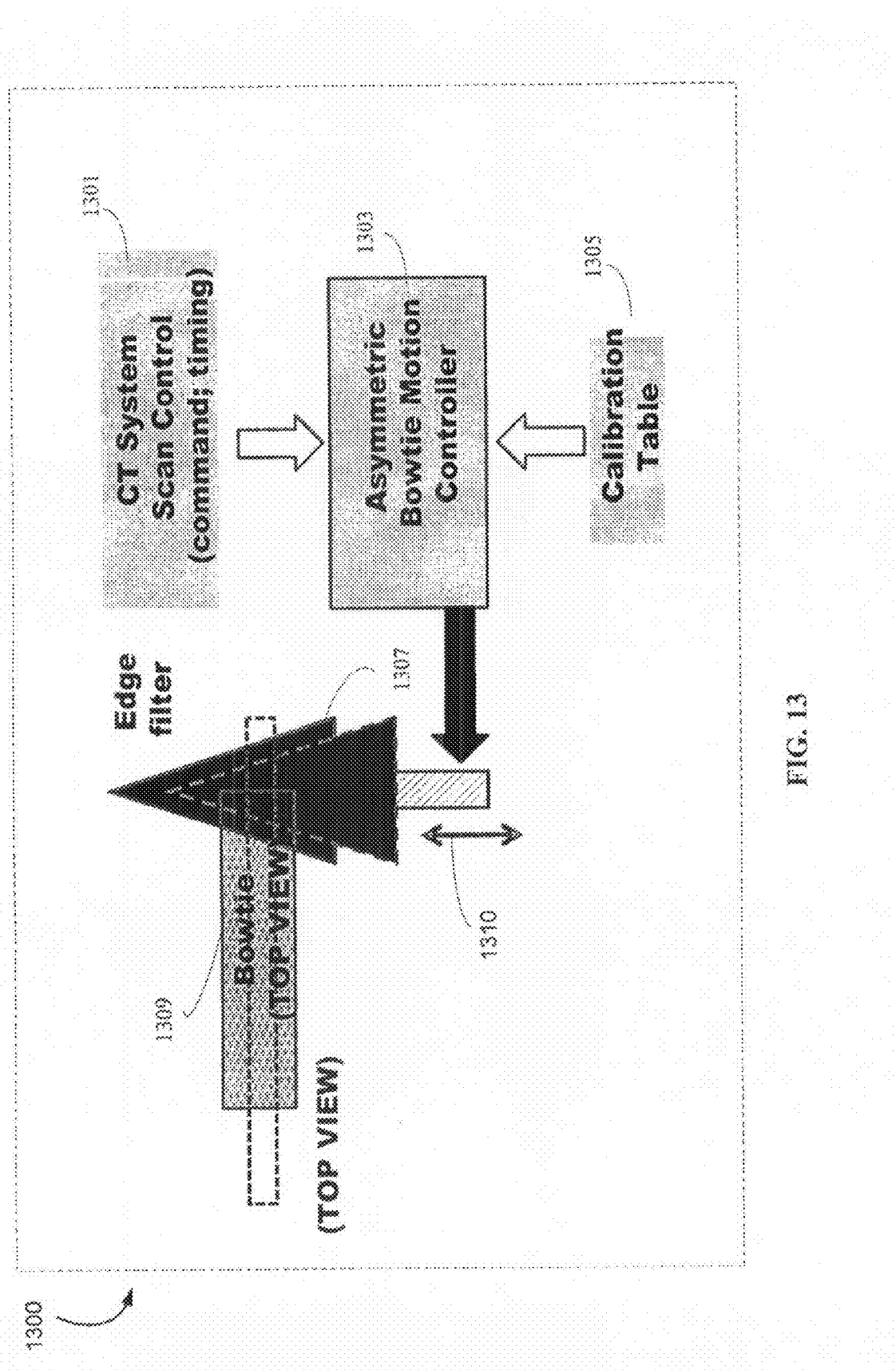
FIG. 13 shows a CT system according to another embodiment controlling a cone-shaped edge filter.

FIG. 13 shows a CT system 1300 according to another embodiment of the disclosure implementing the dynamic control of the asymmetric bowtie filter. The CT controller 1301, the asymmetric bowtie controller 1303, and the calibration table 1305 are configured in a similar manner to that described with reference to FIG. 12.

The CT system 1300 as shown in FIG. 13 depicts a top view of the bowtie filter 1309 and includes a cone-shaped edge filter 1307 that provides rapid change in the attenuation of the asymmetric bowtie filter. The cone-shaped edge filter 1307 can be displaced along a gantry rotational axis in the direction represented by 1310, to achieve rapid changes in the desired attenuation of the asymmetric bowtie filter assembly.

Figure 14:
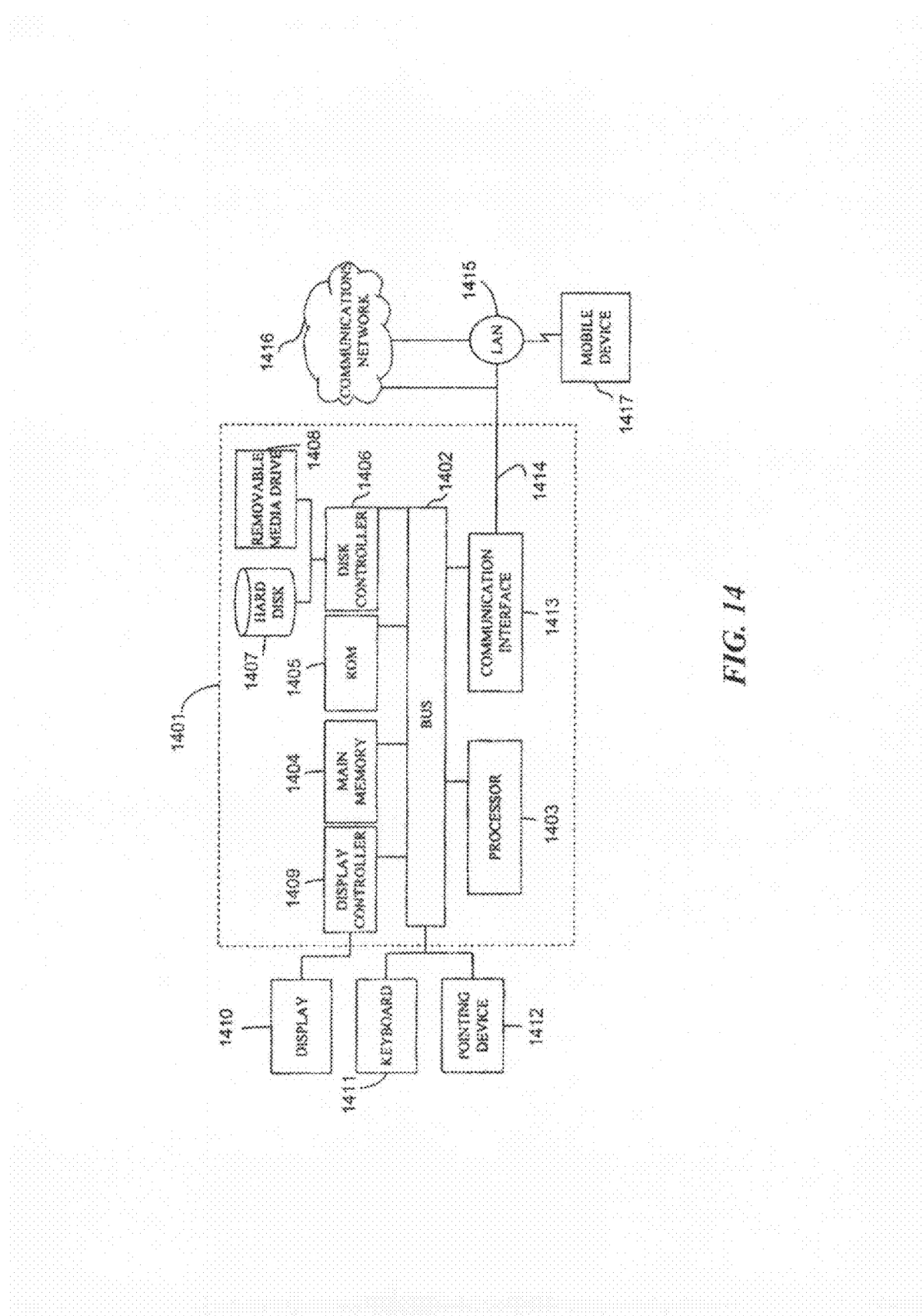
FIG. 14 illustrates a computer system that may be used to control the CT apparatus and upon which embodiments of the present disclosure may be implemented.

The CT apparatus described herein can be controlled using a computer processing apparatus or programmable logic. FIG. 14 illustrates a computer system 1401 that functions as a controller configured to control, for example, motors that engage the CT apparatus. An operator may, for example, set various parameters (e.g., set angle, set linear position, set slew rate, etc.) via a user interface, and a processor (for example, processor 1403) of computer system 1401 may control the apparatus 10 via an interface based on the set parameters.

The computer system 1401 includes a disk controller 1406 coupled to the bus 1402 to control one or more storage devices for storing information and instructions, such as a magnetic hard disk 1407, and a removable media drive 1408 (e.g., floppy disk drive, read-only compact disc drive, read/write compact disc drive, compact disc jukebox, tape drive, and removable magneto-optical drive). The storage devices may be added to the computer system 1401 using an appropriate device interface (e.g., small computer system interface (SCSI), integrated device electronics (IDE), enhanced-IDE (E-IDE), direct memory access (DMA), or ultra-DMA).

The computer system 1401 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1401 may also include a display controller 1409 coupled to the bus 1402 to control a display 1410, for displaying information to a computer user. The computer system includes input devices, such as a keyboard 1411 and a pointing device 1412, for interacting with a computer user and providing information to the processor 1403. The pointing device 1412, for example, may be a mouse, a trackball, a finger for a touch screen sensor, or a pointing stick for communicating direction information and command selections to the processor 1403 and for controlling cursor movement on the display 1410.

The processor 1403 executes one or more sequences of one or more instructions contained in a memory, such as the main memory 1404. Such instructions may be read into the main memory 1404 from another computer readable medium, such as a hard disk 1407 or a removable media drive 1408. One or more processors in a multi-processing arrangement may also be employed to execute the sequences of instructions contained in main memory 1404. In alternative embodiments, hard-wired circuitry may be used in place of or in combination with software instructions. Thus, embodiments are not limited to any specific combination of hardware circuitry and software.

As stated above, the computer system 1401 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1401, for driving a device or devices for implementing the invention, and for enabling the computer system 1401 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1403 for execution. A computer readable medium may take many forms, including but not limited to, non-volatile media or volatile media. Non-volatile media includes, for example, optical, magnetic disks, and magneto-optical disks, such as the hard disk 1407 or the removable media drive 1208. Volatile media includes dynamic memory, such as the main memory 1404. Transmission media, on the contrary, includes coaxial cables, copper wire and fiber optics, including the wires that make up the bus 1402. Transmission media also may also take the form of acoustic or light waves, such as those generated during radio wave and infrared data communications.

Various forms of computer readable media may be involved in carrying out one or more sequences of one or more instructions to processor 1403 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1401 may receive the data on the telephone line and place the data on the bus 1402. The bus 1402 carries the data to the main memory 1404, from which the processor 1403 retrieves and executes the instructions. The instructions received by the main memory 1404 may optionally be stored on storage device 1407 or 1408 either before or after execution by processor 1403.

The computer system 1401 also includes a communication interface 1413 coupled to the bus 1402. The communication interface 1413 provides a two-way data communication coupling to a network link 1414 that is connected to, for example, a local area network (LAN) 1415, or to another communications network 1416 such as the Internet. For example, the communication interface 1413 may be a network interface card to attach to any packet switched LAN. As another example, the communication interface 1413 may be an integrated services digital network (ISDN) card. Wireless links may also be implemented. In any such implementation, the communication interface 1413 sends and receives electrical, electromagnetic or optical signals that carry digital data streams representing various types of information.

The network link 1414 typically provides data communication through one or more networks to other data devices. For example, the network link 1414 may provide a connection to another computer through a local network 1415 (e.g., a LAN) or through equipment operated by a service provider, which provides communication services through a communications network 1416. The local network 1414 and the communications network 1416 use, for example, electrical, electromagnetic, or optical signals that carry digital data streams, and the associated physical layer (e.g., CAT 5 cable, coaxial cable, optical fiber, etc.). The signals through the various networks and the signals on the network link 1414 and through the communication interface 1413, which carry the digital data to and from the computer system 1401 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as un-modulated baseband data through a "wired" communication channel and/or sent within a predetermined frequency band, different than baseband, by modulating a carrier wave. The computer system 1401 can transmit and receive data, including program code, through the network(s) 1415 and 1416, the network link 1414 and the communication interface 1413. Moreover, the network link 1414 may provide a connection through a LAN 1415 to a mobile device 1417 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
a rotating X-ray source;
a plurality of stationary photon-counting detectors configured to capture incident X-ray photons emitted from the X-ray source;
a bowtie filter configured to reduce X-ray reflux;
a movable edge filter configured to reduce the X-ray flux at a leading edge of an X-ray fan beam incident on each photon-counting detector; and
a processor configured to
obtain a scanogram of an object,
compute a voltage and a current value for the X-ray source based on the obtained scanogram,
calculate a flux intensity for each photon-counting detector based on the computed voltage and current of the X-ray source, and
determine a desired position of the edge filter with respect to the bowtie filter based on the calculated flux intensity.

2. The CT apparatus of claim 1, wherein, in determining the desired position of the edge filter, the processor is further configured to compute a minimum required attenuation length of the edge filter to reduce the calculated flux intensity for each photon-counting detector so that each actual flux intensity is lower than a maximum flux threshold that each of the photon-counting detectors can sustain.

3. The CT apparatus of claim 1, wherein the processor is further configured to scan the object using the determined position of the edge filter and normalize the obtained data using a predetermined reference scan.

4. The CT apparatus of claim 1, wherein the processor is configured to determine the desired position of the edge filter as a position that is fixed for each of a plurality of views of the object.

5. The CT apparatus of claim 1, wherein the processor is configured to determine the desired position of the edge filter for each view of a plurality of views of the object.

6. The CT apparatus of claim 1, wherein the processor is further configured to compute a ray angle of a leading edge of an X-ray fan beam incident on each photon-counting detector.

7. The CT apparatus of claim 1, wherein a shape of the edge filter is one of a right-angled triangular filter, a cone-shaped filter, and a circular-shaped filter.

8. The CT apparatus of claim 1, further comprising a bowtie controller configured to receive instructions from the processor and to instruct an electro-mechanical device to move the edge filter to the determined desired position along the edge of the bowtie filter.

9. The CT apparatus of claim 1, further comprising a sensor configured to detect an actual position of the edge filter along the side of the bowtie filter and to transmit the detected actual position to the processor.

10. The CT apparatus of claim 1, further comprising a memory that stores a calibration table that describes a relation between a set position of the edge filter and a corresponding attenuation of the edge filter.

11. The CT apparatus of claim 8, wherein the electro-mechanical device is a stepper motor.

12. The CT apparatus of claim 1, wherein the rotating X-ray source is configured to emit one of a fan-shaped and a cone-shaped X-ray beam.

13. A method for reducing high X-ray flux in a computed-tomography (CT) scanner, the method comprising:
obtaining a scanogram of an object;
computing a voltage and a current value of an X-ray source of the CT scanner based on the obtained scanogram;
calculating a flux intensity for each of a plurality of photon-counting detectors of the CT scanner based on the computed voltage and current values of the X-ray source;
determining a desired position of a movable edge filter with respect to a bowtie filter based on the calculated flux intensity, wherein the movable edge filter reduces X-ray flux at a leading edge of an X-ray fan beam incident on each photon counting detector;
scanning the object scan based on the determined position of the edge filter; and
normalizing the scan of the object with a reference scan.

14. The method of claim 13, wherein the determining step includes determining the desired position of the edge filter as a position that is fixed for each view of a plurality of views of the object.

15. The method of claim 13, wherein the determining step further includes determining the position of the edge filter for each view of the plurality of views of the object.

16. A method for computing a desired position of a movable edge filter with respect to a bowtie filter, the movable edge filter being adjacent to and movable with respect to the bowtie filter, the method comprising:
- defining a maximum flux intensity that a photon-counting detector can sustain;
- calculating a flux intensity at the photon-counting detector and a ray angle of a leading edge of a X-ray fan beam for each view of a plurality of views of an object based on a scanogram and a computed voltage and current of an X-ray source;
- computing an attenuation length of the movable edge filter based on the calculated actual flux intensity; and
- calculating the desired position of the movable edge filter with respect to the bowtie filter based on the computed attenuation length so that the movable edge filter reduces X-ray flux at the leading edge of the X-ray fan beam incident on the photon-counting detector.

17. The method of claim 16, wherein the computing step includes computing the attenuation length of the edge filter to reduce the calculated flux intensity for each view of the plurality of views of the object, so that each actual flux intensity is lower than the defined maximum flux intensity of the photon-counting detector.

18. A non-transitory computer readable medium having stored thereon a program that when executed by a computer, causes the computer to perform the steps of:
- obtaining a scanogram of an object;
- computing a voltage and a current value of an X-ray source of the CT scanner based on the obtained scanogram;
- calculating a flux intensity for each of a plurality of photon-counting detectors of the CT scanner based on the computed voltage and current values of the X-ray source;
- determining a desired position of a movable edge filter with respect to a bowtie filter based on the calculated flux intensity, wherein the movable edge filter reduces X-ray flux at a leading edge of an X-ray fan beam incident on each photon-counting detector;
- scanning the object scan based on the determined position of the edge filter; and
- normalizing the scan of the object with a reference scan.

* * * * *